(12) United States Patent
Abkai

(10) Patent No.: US 10,653,384 B2
(45) Date of Patent: May 19, 2020

(54) METHOD FOR CALIBRATING AN X-RAY IMAGE

(71) Applicant: DENTSPLY SIRONA inc., York, PA (US)

(72) Inventor: Ciamak Abkai, Heddesheim (DE)

(73) Assignee: DENTSPLY SIRONA INC., York, PA (US)

( * ) Notice: Subject to any disclaimer, the term of this patent is extended or adjusted under 35 U.S.C. 154(b) by 183 days.

(21) Appl. No.: 15/781,353

(22) PCT Filed: Dec. 14, 2016

(86) PCT No.: PCT/EP2016/080882
§ 371 (c)(1),
(2) Date: Jun. 4, 2018

(87) PCT Pub. No.: WO2017/102782
PCT Pub. Date: Jun. 22, 2017

(65) Prior Publication Data
US 2018/0360411 A1 Dec. 20, 2018

(30) Foreign Application Priority Data
Dec. 14, 2015 (DE) .......................... 10 2015 225 130

(51) Int. Cl.
*G06K 9/00* (2006.01)
*A61B 6/00* (2006.01)
(Continued)

(52) U.S. Cl.
CPC ............ *A61B 6/582* (2013.01); *A61B 5/0073* (2013.01); *A61B 6/02* (2013.01); *A61B 6/14* (2013.01);
(Continued)

(58) Field of Classification Search
CPC ............ A61B 2505/05; A61B 2576/02; A61B 5/0073; A61B 5/4547; A61B 5/725;
(Continued)

(56) References Cited

U.S. PATENT DOCUMENTS

2006/0212260 A1* 9/2006 Kopelman ........... A61B 5/1077
702/152
2011/0135053 A1* 6/2011 Noordhoek ............ A61B 6/583
378/11
(Continued)

FOREIGN PATENT DOCUMENTS

DE       19620371 A1    12/1997
DE    102008035412 A1     2/2010
(Continued)

*Primary Examiner* — Xin Jia
(74) *Attorney, Agent, or Firm* — Dentsply Sirona Inc.

(57) ABSTRACT

Disclosed is a method for calibrating at least one 2D X-ray image of an object to be imaged, which is recorded by an X-ray device in that X-rays produced by an X-ray source radiate through the object and are recorded by an X-ray detector. An already existing 3D model of a structure of the object is compared to the 2D X-ray image, wherein an actual image positional relationship of the X-ray source and the X-ray detector relative to the object, and/or relative to one another, is determined for the 2D X-ray image.

12 Claims, 2 Drawing Sheets

(51) Int. Cl.
- *G06T 11/00* (2006.01)
- *A61B 5/00* (2006.01)
- *A61B 6/02* (2006.01)
- *A61B 6/14* (2006.01)
- *A61C 9/00* (2006.01)

(52) U.S. Cl.
CPC .......... *A61B 6/5247* (2013.01); *A61C 9/0053* (2013.01); *G06T 11/005* (2013.01); *A61B 5/4547* (2013.01); *A61B 5/725* (2013.01); *A61B 2505/05* (2013.01); *A61B 2576/02* (2013.01); *G06T 2210/41* (2013.01)

(58) Field of Classification Search
CPC ........... A61B 6/02; A61B 6/14; A61B 6/5247; A61B 6/582; A61C 9/0053; G06T 11/005; G06T 2210/41

See application file for complete search history.

(56) References Cited

U.S. PATENT DOCUMENTS

| | | | | |
|---|---|---|---|---|
| 2011/0255765 | A1* | 10/2011 | Carlson | G06T 5/005 382/131 |
| 2014/0270440 | A1* | 9/2014 | Inglese | A61B 6/4241 382/131 |
| 2015/0254816 | A1* | 9/2015 | Carlson | A61B 6/032 382/131 |
| 2017/0325689 | A1* | 11/2017 | Salah | A61C 9/0046 |

FOREIGN PATENT DOCUMENTS

| | | |
|---|---|---|
| DE | 102209008700 A1 | 8/2010 |
| DE | 102011003984 A1 | 8/2012 |

\* cited by examiner

METHOD FOR CALIBRATING AN X-RAY IMAGE

TECHNICAL FIELD

The invention relates to a method for calibrating an X-ray device for the measurement of 2D X-ray images of an object to be imaged, wherein each 2D X-ray image is recorded in that X-rays produced by an X-ray source radiate through the object and are recorded by means of an X-ray detector, wherein a representation of the object in the 2D X-ray image is defined by an actual image positional relationship of the X-ray source and the X-ray detector relative to the object.

STATE OF THE ART

A number of methods for calibrating an X-ray device for three-dimensional measurement, such as a CT X-ray device or a DVT X-ray device are known from the state of the art. DE 102008035412 A1 discloses a method for compiling a dental 3D X-ray image of at least one subarea of an object, wherein the volume is compiled as a 3D X-ray image from a plurality of projection images during one orbit around the object. At least a part of the object is displayed in a visual representation prior to the compilation of the X-ray image, wherein the relative position of the visual representation to the current position of the device and the patient is known. The volume to be imaged, which is a function of the positioning of the object with respect to the device and the selection of the setting and/or control data, is overlaid in the visual representation at least approximately in the correct position, and the setting and/or control data for generating the 3D X-ray image are determined as the position and/or size of the volume to be imaged in the visual representation is changed. The volume to be imaged is overlaid in the visual representation only schematically as an approximate region. The recording angles of the two images can be different. The visual representation can also be an existing 3D image, such as a 3D X-ray image. To overlay the volume to be imaged in the visual representation in a positionally correct manner, a position registration is performed, wherein the relative position of the device to the patient is compared with the current position of the device and the patient in the visual representation in order to correctly display the position of the volume to be imaged in the visual representation.

US 2011/0255765 A1 discloses a system and a method for removing artifacts from X-ray images of the teeth of a patient, wherein the system comprises a surface scanner that generates a surface image of the teeth of the patient. The surface data of the surface image and the volume data of the CT scan are aligned, oriented with respect to one another and overlaid to generate a combined data set. Data points of the volume data that extend beyond the surface of the teeth into the surface data are identified and removed, as a result of which artifacts produced by metal parts are removed.

In one embodiment, the surface model of the surface data is projected to generate forward projection data in the same two-dimensional format as the CT projection data. The forward projection data are combined with the CT projection data to identify the artifacts. Manual pre-positioning of the two sets of projection data relative to one other is not necessary.

In a DVT method, the X-ray tube and a facing digital image sensor are rotated about the object, wherein a plurality of two-dimensional X-ray images are generated from different recording angles during a partial orbit of the X-ray tube. A three-dimensional X-ray image is subsequently reconstructed from the individual two-dimensional X-ray images using a reconstruction method. The correct imaging geometry or image positional relationship of the X-ray tube and the X-ray detector relative to the object is essential for the reconstruction method. Calibration phantoms are typically used to define this image positional relationship. Such calibration measurements are performed when the X-ray device is still in the factory and at regular intervals after the first-time operation of the X-ray device.

One disadvantage of this method is that the original positional relationship defined during calibration can change, for example as a result of wear on the mechanism of the X-ray device or by changing frictional forces in the drives of the X-ray device. As a result of the change in the positional relationship, the actual positional relationship of the X-ray emitter and the X-ray detector relative to the object does not match the predetermined positional relationship derived from the calibration measurement. The reconstruction process is therefore distorted and artifacts such as the blurring of details, stripes and/or shadows can occur in the reconstructed three-dimensional X-ray image. Movement artifacts can also occur if the patient moves during imaging.

Incorrect image positional relationships also cause additional errors in the X-ray images of devices for generating panoramic tomographic images, or in intraoral X-ray images that rely on a known calibrated positional relationship.

The object of the present invention is therefore to provide a method for calibrating an X-ray device that ensures error-free measurement of the object, even without the use of a calibration phantom.

PRESENTATION OF THE INVENTION

The invention relates to a method for calibrating at least one 2D X-ray image of an object to be imaged, which is recorded by an X-ray device in that X-rays produced by an X-ray source radiate through the object and are recorded by means of an X-ray detector. An already existing 3D model comprising a structure of the object is compared to the 2D X-ray image, wherein an actual image positional relationship of the X-ray source and the X-ray detector relative to the object, and/or relative to one another, is determined for the 2D X-ray image.

The 2D X-ray images can be recorded by means of a DVT X-ray device, for example. Therefore, in the course of one orbit, a plurality of 2D X-ray images is generated from different recording angles. The X-ray source is generally rotated 180° to 360° around the object, wherein the X-ray source generates a conical fan of X-rays that is usually pulsed. The X-rays penetrate the three-dimensional object and, for each respective recording angle or respective point in time of the recording, create an attenuated grayscale X-ray image on the X-ray detector as a 2D X-ray image.

The comparison between the existing 3D model and the 2D X-ray image can be performed, for example, by allocating points of the structure in the 3D model to the corresponding points of the structure in the 2D X-ray image.

The determined actual image positional relationship of the X-ray source and the X-ray detector relative to the object or relative to one another can be stored and used for the correction, reconstruction, optimization and/or calculation of later X-ray images.

In this way, the present method for calibration has to be performed once, or at defined intervals, to verify the calibration.

One advantage of this method is that, to measure an object, it is not necessary to first calibrate with a calibration phantom. This reduces the maintenance requirements.

Another advantage of this method is that a calibration is performed for each individual 2D X-ray image via a comparison with the 3D model from a specific recording angle, so that even unanticipated malfunctions of the X-ray device that result in a change in the image positional relationship are corrected immediately.

Another advantage of this method is that it is possible to generate a 3D X-ray image of a patient who is moving during the orbit. The entire lower jaw, for example, can be reconstructed as the imaging structure in sharp focus, without movement artifacts, even in the event of a lateral movement of the head or if the patient is making a chewing movement. This is because the exact image positional relationship of this structure, e.g. a lower jaw, relative to the X-ray source and the X-ray detector is determined by comparing the individual 2D X-ray images with the virtual projection of the 3D model in the virtual 2D projection image. The calibration with respect to the displayed structure of the object, such as a lower jaw, is thus determined in the best possible manner, despite the movement of the patient.

When comparing the 3D model with the 2D X-ray image, a virtual 2D projection image is generated by applying a virtual projection method to at least one part of the 3D model and taking into account a predetermined image positional relationship, wherein the structure in the 2D X-ray image is compared with the structure in the virtual 2D projection image.

In the virtual projection method, therefore, the imaging geometry for the respective 2D X-ray image is simulated with the aid of a computer, thereby generating the corresponding virtual 2D projection image. In the projection method, the image positional relationship of a virtual X-ray source and a virtual X-ray detector relative to the 3D model of the structure is thus simulated, wherein the manner in which the X-rays in the form of a conical fan virtually radiate through and display the 3D model on the virtual X-ray detector is simulated. The result of this is that, with the same image positional relationship, the shape of an image of the structure in the 2D X-ray image matches a virtual projection of the structure in the virtual 2D projection image.

In an alternative method, the comparison between the 3D model and the 2D X-ray image can be performed by applying a virtual back projection method to the 2D X-ray image, wherein the 2D X-ray image is then displayed in a 3D space. This projection is subsequently compared with the existing 3D model.

Deviations are identified when the structure in the 2D X-ray image is compared with the virtual 2D projection image, wherein the image positional relationship is incrementally changed within the framework of an optimization method, and a new virtual 2D projection image is generated after each change until the deviations are smaller than a defined threshold value.

The predetermined image positional relationship of the X-ray source and the X-ray detector relative to the object can be from a calibration, or a later calibration, or it can be determined mathematically on the basis of a model. The predetermined image positional relationship is thus a starting solution, based on which the actual image positional relationship is determined using the optimization method. A so-called Kalman filter can be used for the optimization method, by means of which starting solutions are stabilized. A Kalman filter is used to remove interference caused by measuring devices.

The threshold value is defined in such a way that, when this threshold value is undershot, the structure in the 2D X-ray image corresponds as much as possible to the virtual 2D projection image, so that the determined image positional relationship after the end of the optimization method corresponds, or is at least similar, to the actual image positional relationship of the respective 2D X-ray image in relation to the structure of the displayed object.

The comparison can be performed with the aid of a comparison operator. The comparison operator is then optimized with the optimization method. The optimization method can, for example, be concluded after a predetermined threshold value has been reached. The threshold value of the quality precision of the optimization can be 10% of the calibration precision of the respective X-ray device, for example.

The optimization method can either directly optimize the comparison operator or optimize the deviations between the structures in the virtual 2D projection image and the 2D X-ray image.

The 2D X-ray images can advantageously be recorded step-by-step from different recording angles during a movement of the X-ray source and the X-ray detector around the object, wherein, by using a reconstruction method and knowing the determined actual image positional relationships of the 2D X-ray images, a 3D X-ray image of the object, or a panoramic tomographic image of the object, is generated from the recorded 2D X-ray images.

The movement of the X-ray source and the X-ray detector around the object can be a circular rotation in the form of a partial orbit about the object or, by varying the orientation and position of the X-ray source and X-ray detector in relation to the object, it can also be a different movement.

Consequently, the present method can be used for the calibration of a DVT X-ray device or a CT X-ray device. The calibration of the image positional relationship is thus verified and corrected for each individual 2D X-ray image. This therefore makes dynamic verification possible, so that even sudden mechanical disturbances of the device are taken into account. In the reconstruction method, the grayscale image in the 2D X-ray image corresponds to the sum of the absorptions along a measured X-ray path through the object. The X-ray path is then broken down into small voxels. In the back projection, the measured value along each measured X-ray path is respectively distributed as well as possible to the voxels located along said path. For the 2D X-ray images this is done from a variety of recording angles, so that a good estimation of the 3D X-ray image of the displayed object is obtained as a result.

For the reconstruction of a panoramic tomographic image, a panoramic tomographic image is calculated from the 2D X-ray images taken from different recording directions using a computer.

The starting solution is thus a planned path of the X-ray source and the X-ray detector around the object, which can also be taken from a factory calculation, for example. This path, which connects the individual positions of the X-ray source and the X-ray detector relative to the object for the individual recording angles, is then optimized or incrementally defined more precisely in the course of the optimization method until the actual path is determined. The actual path is then used for the reconstruction, so that the error-free 3D X-ray image or a panoramic tomographic image is reconstructed.

The structure of the object can advantageously be an upper jaw, a lower jaw, a group of teeth, a dental prosthesis part, a filling, an inlay, the entire object, a part of the object, the head of a patient and/or an individual tooth.

The object can therefore also be a part of a jaw consisting of a plurality of teeth and a dental prosthesis part.

The existing 3D model of the structure can advantageously be recorded by means of an optical three-dimensional surface measurement method, wherein the 3D model includes only one surface of the structure. During the comparison, a surface edge of the structure in the 2D X-ray image is then compared with a surface edge of the structure in the virtual 2D projection image.

The existing 3D model of the structure can comprise the entire surface of the structure or even only a part of the surface of the structure. When measuring with the aid of a three-dimensional surface scanner, for example, only the visible surfaces of the teeth can be measured. The surface measurement method can, for example, be a fringe projection method, a confocal measurement method or a laser scanning method. The surface edge of the structure, which can be compared with the surface edge of the structure in the 2D X-ray image, thus emerges in the virtual projection of the 3D model. The edge of the teeth, for example, or even the depressions of the teeth which are clearly visible in the 2D X-ray images, can be used for the comparison.

The existing 3D model can also only depict a point cloud which represents the surface or distinctive points of the structure.

The existing 3D model of the structure can advantageously be generated by recording an impression of the structure with the aid of an optical three-dimensional surface measurement method, wherein the 3D model includes only one surface of the structure, wherein, during the comparison, a surface edge of the structure in the 2D X-ray image is compared with a surface edge of the structure in the virtual 2D projection image.

Consequently, only one impression of the structure is measured, so that the surface of said structure is determined therefrom. The impression of one or more teeth, for example, can be measured.

The existing 3D model of the structure can advantageously be recorded by means of a three-dimensional volume measurement method, in particular by means of an MRI method, CT method or DVT method, and contains volume data of the structure, wherein, for the comparison, the structure in the 2D X-ray image is compared with the simulated projection of the structure in the virtual 2D projection image.

The 3D model can therefore also comprise volume data with information about the internal composition of the structure. Substructures within the structure, e.g. the separating surface between a tooth and the surrounding gum, or the shape of the tooth roots or the jaw bone, can thus also be used for the comparison.

The magnetic resonance imaging method (MRI) is physically based on the principle of nuclear magnetic resonance, wherein the separating surface between soft tissue and hard tissue, such as between teeth and the surrounding gum, is displayed more clearly than in a 3D X-ray image.

The computed tomography method (CT) is based on a reconstruction of a 3D X-ray image from individual 2D X-ray images of the object from different recording angles, wherein a multirow detector is used as the X-ray detector.

In digital volume tomography (DVT), the 3D X-ray image is likewise reconstructed from the individual 2D X-ray images from different recording angles, wherein a flat panel detector is used as the X-ray detector.

Advantageously, in the projection method, not only the image positional relationship of the X-ray source and the X-ray detector relative to the object is taken into account for the virtual projection method, but also the thickness of the structure to be imaged and thus the X-ray attenuation by the structure and/or the material of the structure. The X-ray attenuation dependent thereon is therefore taken into account as well. That is to say, the comparison of a virtual projection image and a 2D X-ray image is not restricted only to the edge of a structure, but also includes additional image contents.

Therefore, by taking into account the thickness and the material of the structure, an improved simulation of the projection in the virtual 2D projection image is possible. During the measurement of the structure by means of an optical surface scanner, it is possible to determine, for example, whether the structure is a natural tooth, or a dental prosthesis part made of ceramic, gold or plastic. The respective factor for the X-ray attenuation for gold, plastic or ceramic is thereby taken into account.

When implementing the optimization method, the predetermined image positional relationship from a known factory calibration can advantageously be used as a starting solution.

Consequently, a starting solution that is already very close to the actual image positional relationship is used.

As a result, the amount of time and the computing effort needed for the optimization method are reduced.

When comparing the 2D X-ray image with the virtual 2D projection image, a degree of similarity is advantageously calculated for the determination of the deviations, wherein a gradient difference method, a direct difference method, a correlation method, a cross-correlation method of the first and/or a higher order, a statistical method or a method of least-squares errors is used.

When using the mentioned methods, matching patterns in the 2D X-ray image and in the virtual 2D projection image, such as e.g. the edge of the teeth, are compared with one another to determine the actual image positional relationship. The degree of similarity increases as the similarity of these patterns increases. When the image positional relationship in the 2D X-ray image and in the simulated 2D projection image match, the patterns should match or at least partially resemble one another. In this case, therefore, the degree of similarity is at its maximum, so that the optimization method can be concluded.

The statistical method can be a so-called mutual information method, for example.

By using the optimization method, the degree of similarity can advantageously increase and the deviations can decrease until an optimum, and with it the actual image relationship, is determined.

As a result, when using the optimization method, the solutions for the image relationship approach the optimum solution.

The change of the image positional relationship in the course of the optimization method can advantageously be described by means of a transformation matrix.

By using the transformation matrix, the 3D model can thus be virtually offset or rotated incrementally relative to the X-ray source and to the X-ray detector.

A first structure of the object can advantageously be selected in a first step to determine the first actual image positional relationships of the 2D X-ray images for this first structure according to the present method, wherein a second structure of the object is selected in a second step to determine the second actual image positional relationships of the 2D X-ray images for this second structure according to the present method.

The corresponding actual image positional relationships for the respective selected structure are thus determined.

A first 3D X-ray image can advantageously be reconstructed using the first actual image positional relationships and a second 3D X-ray image can be reconstructed using the second actual image positional relationships, wherein a first region in the first 3D X-ray image, which displays the first structure in sharp focus, is subsequently merged with a second region in the second 3D X-ray image, which displays the second structure in sharp focus, to one overall 3D X-ray image of the object.

As a result, therefore, at least the selected structure is displayed in sharp focus in the corresponding 3D X-ray image of this structure.

The first structure can advantageously be a lower jaw or a part of the lower jaw and the second structure can be an upper jaw or a part of the upper jaw.

The first 3D X-ray image is thus generated with the lower jaw as the selected structure, so that, even in the event of a movement of the lower jaw during the recording, the lower jaw is displayed in sharp focus, while the upper jaw and the rest of the head of the patient are blurry. In the second 3D X-ray image, the upper jaw and the rest of the head of the patient are accordingly displayed in sharp focus, while the lower jaw is blurry. The sharp regions of the two 3D X-ray images can then be merged to one overall 3D X-ray image, which shows both the lower jaw and the upper jaw in sharp focus.

BRIEF DESCRIPTION OF THE DRAWINGS

The invention is explained with reference to the drawings. The drawings show.

DESIGN EXAMPLES

Figure 1:
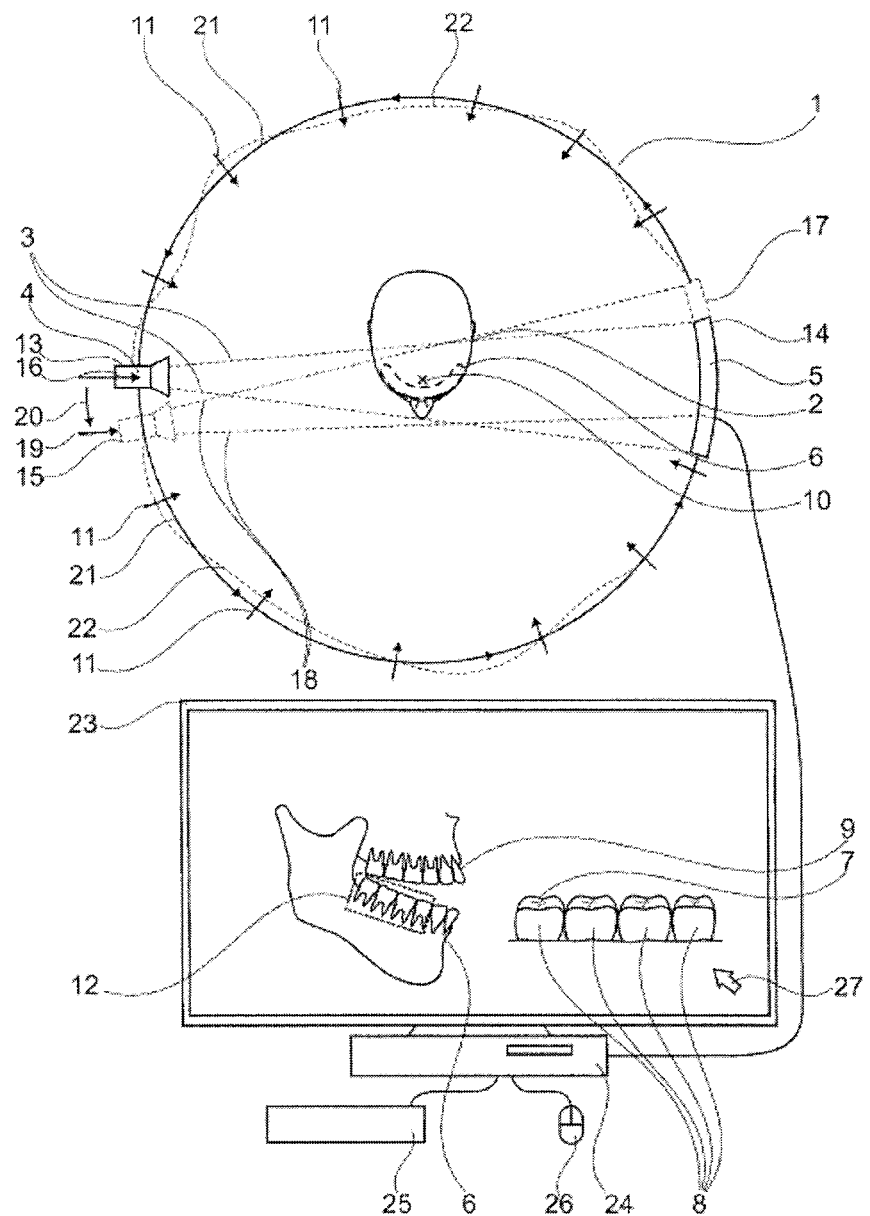
FIG. 1 a sketch to illustrate the present method.

FIG. 1 shows a sketch to illustrate the present method for calibrating an X-ray device 1 for the measurement of 2D X-ray images of an object 2 to be imaged, such as the head of a patient. Each 2D X-ray image is recorded in that X-rays 3 in the form of a cone-shaped fan produced by an X-ray source 4 radiate through the object 2 and are recorded by means of an X-ray detector 5, such as a flat panel detector. The object 2 contains a structure 6 to be imaged, such as a lower jaw, which is indicated with dashed lines. A 3D model 7 already exists for the structure 6 to be imaged, i.e. the lower jaw, which has been recorded by means of an optical three-dimensional surface measurement method. In the present case, the existing 3D model 7 includes only four molars 8 on the right side of the lower jaw 6. The 3D model can, for example, be recorded by means of a handheld 3D dental camera based on a fringe projection method or a confocal measurement method. The 3D model can also be generated by first taking an impression of the teeth 8 and then measuring this impression with the aid of the handheld dental camera. The 3D model 7 thus only includes visible surfaces of the molars 8. During the measurement of a 3D X-ray image 9, the X-ray source 4 and the X-ray detector 5 are incrementally rotated about a rotation point 10 within a measuring volume, wherein individual 2D X-ray images of the object 2 and thus of the structure 6 are recorded from different recording angles 11 represented by arrows, wherein the 3D X-ray image 9 of the object is generated from the recorded 2D X-ray images from the different recording angles 11 by using a reconstruction method. A subarea 12 of the structure 6 to be imaged, i.e. the lower jaw, is indicated in the 3D X-ray image 9 with dashed lines. A predetermined image positional relationship 13 of the X-ray source 4 is indicated with a solid line. Across from that, a predetermined image positional relationship 14 of the X-ray detector 5 is likewise indicated with a solid line. An actual image positional relationship 15 of the X-ray source 4 for the respective recording angle 16 is indicated offset thereto with a dashed line. A likewise offset actual image positional relationship 17 of the X-ray detector 5 is also indicated with a dashed line. The X-rays 18 in the form of a conical beam cone are accordingly likewise offset and record the object 2 from an actual recording angle 19, which deviates significantly from the predetermined recording angle 16. This deviation can be caused by the mechanism or the drives coming out of alignment, for example, and by increasing frictional forces in the drives of the X-ray device 1. The present method therefore serves to compensate for this offset, which is indicated by the arrow 20. This offset between the predetermined image positional relationship 13, 14 and the actual image positional relationship 15, 17 can also take place in radial direction relative to the rotation point 10. The individual image positional relationships 13 of the X-ray source 4 and the predetermined image positional relationships 14 of the X-ray detector 5 for all recording angles 11 then form an orbital path 21, which is indicated by a solid line. After the implementation of the optimization method for each individual recording angle 11, the actual image positional relationships 15 of the X-ray source 4 and the actual image positional relationships 17 of the X-ray detector 5, which form an actual orbital path 22 indicated with a dashed line, are determined. The deviations between the predetermined orbital path 21 and the actual orbital path 22 can be caused not only by disturbances in the drive mechanism, but also by movements of the patient during an orbit. Therefore, in an original reconstruction using the predetermined orbital path 21, which can be predefined by a factory calibration, for example, a blurry 3D X-ray image is reconstructed, which in particular displays a blurred image of the structure 6 to be imaged because it contains interference artifacts. In a reconstruction using the determined actual orbital path 22, a 3D X-ray image 9 is generated, which in particular displays the details and the structure 6 to be imaged, e.g. the lower jaw, clearly and in sharp focus. The 3D X-ray image 9 and the 3D model 7 are displayed by means of a display device 23, such as a monitor. The image data of the X-ray detector 5, such as the individual 2D X-ray images, are transmitted to a computer 24 via cable or wirelessly. The reconstruction method and the optimization method are also carried out by means of the computer 24. The computer 24 is connected to the input means, such as a keyboard 25 and a mouse 26, to allow a user to navigate with the aid of a cursor 27.

Figure 2:
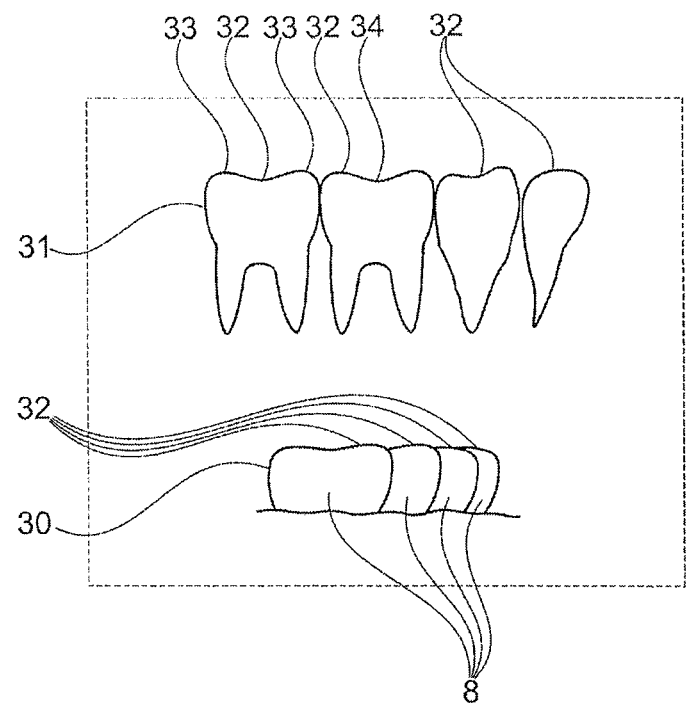
FIG. 2 a sketch to illustrate the optimization method for the starting solution, FIG. 3 a sketch to illustrate the optimization method for the final solution.

FIG. 2 shows a sketch to illustrate the optimization method. By applying a projection method to the 3D model 7 from FIG. 1 and taking into account the predetermined image positional relationship 13 of the X-ray source 4 and the predetermined image positional relationship 14 of the X-ray detector 5 for the recording angle 16, a virtual 2D projection image 30 is generated. The X-ray irradiation of the virtual 3D model 7 is therefore virtually simulated by irradiating the 3D model 7 with a virtual X-ray source and, after simulated X-ray absorption, displaying the 2D projection image 30 on a virtual X-ray detector. The actual 2D X-ray image 31 from the actual recording angle 19 is displayed for comparison. In this case, only the subarea 12 with the molars 8 is displayed. It is clearly visible that the 2D projection image 30 of the 3D model 7, and thus of the molars 8, deviates significantly in its form from the associated 2D X-ray image 31. This is caused by the offset 20 between the predetermined recording angle 16 and the actual recording angle 19. In particular the tooth edges 32 can be used for the comparison method, because they are visible in both the 2D projection image 30 and in the 2D X-ray image 31. Characteristic structures, such as tooth cusps 33 and tooth depressions 34, can be used for the comparison method as well. For the comparison method, a degree of similarity is determined which is a reliable measure of the similarity between two structures. The comparison method can be carried out automatically with the aid of the computer 24 of FIG. 1.

Figure 3:
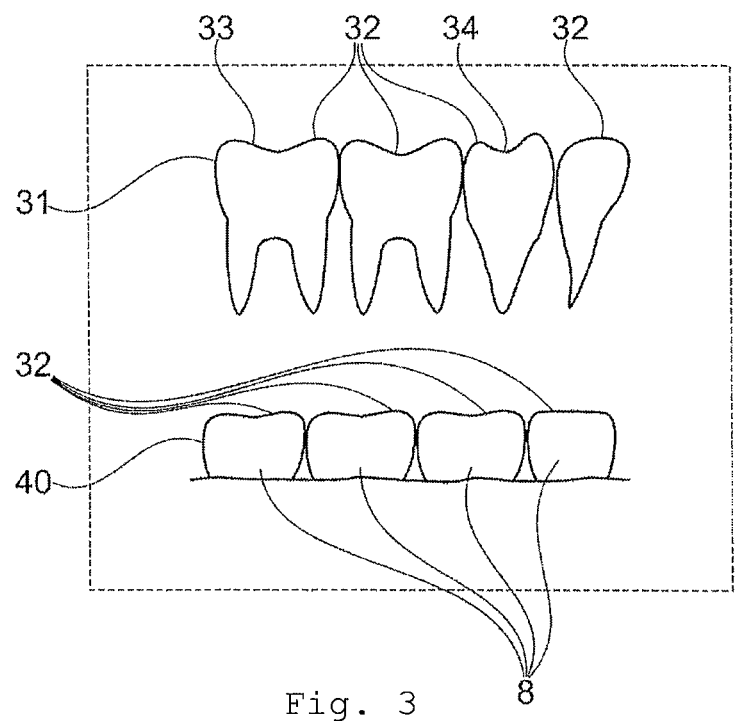

FIG. 3 shows a sketch to illustrate the optimization method, wherein, in comparison to FIG. 2, an actual 2D projection image 40 is generated by using the projection method and with the aid of the actual positional relationship 15 of the virtual X-ray source and the actual image positional relationship 17 of the virtual X-ray detector from FIG. 1. When compared with the 2D X-ray image 31, it is now clear that the shapes of the tooth edges 32, the tooth cusps 33 and the tooth depressions 34 of the teeth 8 match. Any deviation of the geometric image positional relationship, on the basis of which the virtual projection image has been calculated, thus leads to a result that exhibits a lower degree of similarity between the structures in the virtual production image and the 2D X-ray image. The degree of similarity thus reaches its maximum, so that the optimization method can be concluded and the actual image positional relationship of the X-ray source and the X-ray detector has been determined. The optimization method proceeds in a stepwise manner from a starting solution in FIG. 2 to a final solution in FIG. 3. The change 20 between the predetermined image positional relationship 13 and the actual image positional relationship 15 can, for example, be described with the aid of a transformation matrix.

REFERENCE SIGNS

1 X-ray device
2 Object to be imaged
3 X-rays
4 X-ray source
5 X-ray detector
6 Structure to be imaged
6 Lower jaw
7 3D model
8 Molars
9 3D X-ray image
10 Rotation point
11 Recording angle
12 Subarea
13 Predetermined image positional relationship
14 Predetermined image positional relationship
15 Actual image positional relationship
16 Recording angle
17 Actual image positional relationship
18 X-rays
19 Actual recording angle
20 Arrow
20 Offset
21 Predetermined orbital path
22 Actual orbital path
23 Display device
24 Computer
25 Keyboard
26 Mouse
27 Cursor
30 Virtual 2D projection image
31 Actual 2D X-ray image
32 Tooth edges
33 Tooth cusps
34 Tooth depressions
40 Determined virtual 2D projection image

The invention claimed is:

1. Method for calibrating at least one 2D X-ray image of an object to be imaged, which is recorded by means of an X-ray device in that X-rays produced by an X-ray source radiate through the object and are recorded by means of an X-ray detector, wherein an already existing 3D model comprising a first structure of the object is compared to the 2D X-ray image, wherein an actual image positional relationship of the X-ray source and the X-ray detector relative to the object, and/or relative to one another, is determined for the 2D X-ray image, wherein for the comparison of the 3D model with the 2D X-ray image and taking into account a predetermined image positional relationship, a virtual 2D projection image is produced by applying a virtual projection method to at least one part of the 3D model, wherein the first structure in the 2D x-ray image is compared to the first structure in the virtual 2D projection image, wherein deviations are identified during the comparison of the first structure in the 2D X-ray image with the virtual 2D projection image, wherein the image positional relationship is incrementally changed within the framework of an optimization method, and a new virtual 2D projection image is generated after each change until the deviations are smaller than a defined threshold value.

2. The method according to claim 1, wherein the 2D X-ray images are recorded step-by-step from different recording angles during a movement of the X-ray source and the X-ray detector around the object, wherein by using a reconstruction method and knowing the determined image positional relationships of the 2D X-ray images, a 3D X-ray image of the object, or a panoramic tomographic image of the object, is generated from the recorded 2D X-ray images.

3. The method according to claim 1, wherein the first structure of the object is an upper jaw, a lower jaw, a group of teeth, a dental prosthesis part, a filling, an inlay, the entire object, a part of the object, a head of a patient and/or an individual tooth.

4. The method according to any of claim 1, wherein the existing 3D model of the first structure is recorded by an optical three-dimensional surface measurement method, wherein the 3D model includes only one surface of the first structure, wherein during the comparison, a surface edge of the first structure in the 2D X-ray image is compared with a surface edge of the first structure in the virtual 2D projection image.

5. The method according to any of claim 1, wherein the existing 3D model of the first structure is generated by recording an impression of the first structure with the aid of an optical three-dimensional surface measurement method, wherein the 3D model includes only one surface of the structure, wherein during the comparison, a surface edge of the structure in the 2D X-ray image is compared with a surface edge of the structure in the virtual 2D projection image.

6. The method according to claim 1, wherein the existing 3D model of the first structure has been recorded by means of a three-dimensional volume measurement method, and contains volume data of the structure, wherein for the comparison, the structure in the 2D X-ray image is compared with the simulated projection of the structure in the virtual 2D projection image.

7. The method according to claim 1, wherein in the virtual projection method, not only the image positional relationship of the X-ray source and the X-ray detector relative to the object, but also the thickness of the first structure to be imaged and thus the X-ray attenuation by the structure and/or the material of the first structure, as well as the X-ray attenuation dependent thereon, are taken into account.

8. The method according to claim 1, wherein for the implementation of the optimization method, the predetermined image positional relationship from a known calibration is used as the starting solution.

9. The method according to claim 1, wherein when comparing the 2D X-ray image with the virtual 2D projection image, a degree of similarity is calculated for the determination of the deviations, wherein a gradient difference method, a direct difference method, a correlation method, a cross-correlation method of a first and/or a higher order, a statistical method or a method of least-squares errors is used.

10. The method according to claim 1, wherein a first structure of the object is selected in a first step to determine first actual image positional relationships of the 2D X-ray images for this first structure, wherein a second structure of the object is selected in a second step to determine second actual image positional relationships of the 2D X-ray images for the second structure.

11. The method according to claim 10, wherein a first 3D X-ray image is reconstructed using the first actual image positional relationships and a second 3D X-ray image is reconstructed using the second actual image positional relationships, wherein a first region in the first 3D X-ray image, which displays the first structure in sharp focus, is subsequently merged with a second region in the second 3D X-ray image, which displays the second structure in sharp focus, to one overall 3D X-ray image of the object.

12. The method according to claim 10, wherein the first structure is a lower jaw or a part of the lower jaw and the second structure is an upper jaw or a part of the upper jaw.

* * * * *